United States Patent
Illmensee et al.

(10) Patent No.: US 6,762,033 B2
(45) Date of Patent: Jul. 13, 2004

(54) METHOD FOR DETERMINING THE FERTILITY OF MAMMALS, ESPECIALLY HUMANS

(75) Inventors: Karl Oskar Illmensee, Innsbruck (AT); Hans Dieplinger, Innsbruck (AT)

(73) Assignee: Vitateq Biotechnology GmbH, Innsbruck (AT)

( * ) Notice: Subject to any disclaimer, the term of this patent is extended or adjusted under 35 U.S.C. 154(b) by 0 days.

(21) Appl. No.: 10/028,234

(22) Filed: Dec. 21, 2001

(65) Prior Publication Data
US 2002/0055182 A1 May 9, 2002

Related U.S. Application Data

(63) Continuation of application No. PCT/AT00/00171, filed on Jun. 21, 2000.

(30) Foreign Application Priority Data

Jun. 25, 1999 (AT) .............................................. 1119/99

(51) Int. Cl.[7] .............................................. G01N 33/53
(52) U.S. Cl. ...................... 435/7.9; 435/7.21; 435/7.72; 436/510; 436/517; 436/518; 436/808; 436/65
(58) Field of Search ............................. 435/7.21, 7.72, 435/7.9; 436/510, 517, 518, 808, 65

(56) References Cited

FOREIGN PATENT DOCUMENTS

WO        WO95/27059    * 10/1995

OTHER PUBLICATIONS

L. Jerkovic et al, "Afamin and vitamin E in follicular fluid of patients undergoing IVF", Human Reproduction, 14 (Abstract Book 1): 203–204, Abstracts of the 15th Annual Meeting of the Federation Francaise pour 1' Etude de la Reproduction Tours, Jun. 1999.*

L. Jerkovic et al, "Afamin and vitamin E in Follicular Fluid, In ejaculate, and in the plasma of IVF–Patients", Reproduction in Domestic Animals, Vol 32, No. SUP 4, 114 (1997).*

Jerkovic et al., "Afamin and vitamin E in follicular fluid of patients undergoing IVF," Human Reproduction, 14(Abstract Book 1):203–204, Abstracts of the 15th Annual Meeting of the Federation Francaise pour l'Etude de la Redproduction Tours, Jun. 1999.

Lichenstein et al., "Afamin is a new member of the albumin, α–fetoprotein, and vitamin D–binding protein gene family," J. Biological Chemistry, 269:18149–18154, 1994.

Lichenstein et al., "Afamin is a new member of the albumin, α–fetoprotein, and vitamin D–binding protein gene family," Chemical Abstracts, 121(15):430, Abstract No. 173290q, 1994.

* cited by examiner

Primary Examiner—Long V. Le
Assistant Examiner—Deborah A Davis
(74) Attorney, Agent, or Firm—Fulbright & Jaworski L.L.P.

(57) ABSTRACT

Disclosed is a method for determining the fertility of mammals, in particular of humans, wherein
 a body or organ fluid is taken from a mammal,
 the afamin content is determined in this body or organ fluid, and
 the determined afamin content is compared with a reference value so as to determine the fertility,
the use of afamin for determining the fertility of mammals, as well as a kit for carrying out this method.

21 Claims, 4 Drawing Sheets

METHOD FOR DETERMINING THE FERTILITY OF MAMMALS, ESPECIALLY HUMANS

This application is a continuation of PCT Application No. PCT/AT00/00171 filed Jun. 21, 2000, which claims priority to Austrian Application No. A 1119/99 filed Jun. 25, 1999.

The invention relates to a method for determining the fertility of mammals, in particular of humans.

Due to the increase in the knowledge and abilities concerning the in vitro-fertilization technique, the demand of reliable and also low-cost fertility determining methods has highly increased. What is involved is not merely the basic diagnosis of fertility disturbances as such, but increasingly also the detection of the degrees of fertility and the determination of the fertilization and/or nidation of the fertilized oocytes.

Afamin is a 87 kDa protein belonging to the albumin group and having many things in common, structurally and in terms of biochemistry, with the proteins of this group, such as, e.g., with human serum albumin, human α-fetoprotein or human vitamin D binding protein. Afamin has already been cloned and sequenced and thus is also available in recombinant form (WO 95/27059).

Moreover, biochemical and physiological tests have shown that this protein has vitamin E-binding properties. It could be demonstrated that afamin occurs not only in blood, but also in other body and organ fluids, such as, e.g., cerebrospinal, follicular and seminal fluid.

The present invention has as its object to provide a completely novel fertility determination method.

According to the invention, this object is achieved by a method for determining the fertility of mammals, in particular humans, which is characterized in that a body or organ fluid is taken from a mammal, the afamin content is determined in this body or organ fluid, and the determined afamin content is compared with a reference value so as to determine the fertility.

The present invention is based on the surprising finding that the afamin concentration in the various body or organ fluids, where afamin is present, directly correlates with the fertility properties. This correlation is not merely restricted to the presence of fertility disturbances, but is also possible for diagnosing fertility fluctuations or pregnancies. According to the invention, it has even been shown that apart from the detection of the presence or absence of oocytes via the methodology according to the invention for determining the afamin content, even an evaluation of the degree of maturity of oocytes is possible.

The present invention may be used in human medicine, in particular in the monitoring of in vitro fertilizations or in fertilization diagnoses and expert opinions. Yet it also has enormous possibilities within the scope of modern animal breeding, since it is easy to standardize and does not require complicated laboratory equipment for carrying out the tests.

Afamin is present in many different body or organ liquids, and it has been shown according to the invention that the afamin content in all these fluids correlates with the fertility properties. According to preferred embodiments of the present invention, however, the afamin content is primarily determined in body or organ fluids which are characterized by a high physiological afamin content, such as, e.g., serum, follicular or seminal fluid. Yet it is, of course, also possible to carry out the method according to the invention with other body or organ fluids, such as cerebrospinal fluid, since the concentration of afamin in these other fluids also lies in a range which, as a rule, does not cause any problems in terms of the possible afamin detection limit.

In practice, the method according to the invention may be carried out in any manner desired, primarily as regards the manner of taking the body or organ fluid or as regards the determination of the afamin content. The afamin content may, e.g. be determined immunologically, electrophoretically or chromatographically. According to the invention, immunological determination methods often are preferred for afamin, since not only a series of different monoclonal antibodies are available against different epitopes of afamin, but because it is particularly immunological tests, such as in the form of standard ELISA tests, which are easy to design such that they can also be carried out and evaluated without any complex laboratory instruments (e.g. in combination with calorimetric detection methods). In this manner it is possible to provide the determination method according to the invention also in a form which is easy to carry out for common people.

As the reference value, usually an afamin normal value for the respective body or organ fluid is used. In the present method, this may, e.g., be obtained in the form of comparative values, comparative curves or comparative tables or—as is generally preferred—by a simultaneous determination of a reference sample (having a defined afamine content) together with the sample of the body or organ fluid taken. In the latter instance, the systematic error possibly resulting from using different determination methods of different determination conditions, which probably can never be completely eliminated, is avoided right from the beginning. This may be particularly important in determinations where merely gradual differences in afamin contents (e.g. when determining the degree of maturity of oocytes) are at issue.

Preferably, the sample measured according to the invention is not only compared with one reference value, but it is compared with two or more reference values. Thus it is, e.g., possible to provide a different reference value or a reference sample, such as, e.g., a "pathological" reference or a "pregnancy" reference, etc., besides a "normal value".

According to the invention, however, it is preferred to provide a reference value for the afamin content in the corresponding body or organ fluid which corresponds to the afamin content of a normal patient (or, in animal breeding, to the sample of the normal animal).

When carrying out the method according to the invention, this reference value preferably is obtained in that the afamin content of a reference sample is determined in parallel with the fertility determination of the sample.

According to the invention, the determination of the afamin content preferably is effected by using immunological methods, in particular by using a monoclonal antibody, since by this standardizing can be achieved very efficiently and also for the most varying lots of a determination kit, the data found will be compatible among themselves.

According to the invention it has been shown that particularly in the seminal and follicular fluid, beside the afamin content, also the vitamin E content directly correlates with the fertility property and thus likewise may be employed for the method according to the invention. Thus, the method according to the invention preferably is further combined with a determination of the vitamin E content in the respective body or organ fluid, which vitamin E content then optionally also will be compared with a reference value.

Numerous methods of determining vitamin E in body or organ fluids have been described. As in the determination of the afamin content within the scope of the present invention, the specific manner in which the vitamin E content is determined likewise is not critical for the present invention, yet HPLC or other biochemical methods are the preferred methods of determining vitamin E concentrations.

In a further aspect, the present invention relates to the use of afamin for determining the fertility properties of mammals.

A further aspect of the present invention relates to a kit for determining the fertility of mammals, which comprises a sample of a body or organ fluid from a mammal, or a vessel for receiving the body or organ fluid, a reagent for detecting the afamin content in the sample, and afamin reference means.

As mentioned above, the choice of the reagent for detecting the afamin content will, of course, depend on the respective detection methodology used. For instance, the reagent for detecting the afamin content preferably comprises an antibody to afamin, in particular a monoclonal afamin antibody. Preferably, this afamin antibody also comprises further detection means, such as fluorescent, radioactive or chromogenic groups, or it may be bound by other detection means (e.g., by secondary antibodies).

The afamin reference means preferably comprise a standardized amount of afamin, such as a reference sample of the respective body or organ fluid. On the other hand, the afamin reference means may, however, also consist in a simple comparative value or a comparative table or a comparative curve, respectively, which preferably is standardized for the respective body or organ fluid and the respective detection methodology.

A kit according to the invention is particularly preferred which comprises a whole series of standardized afamin samples, which defined a calibration line, e.g., or which are representative of certain fertility features.

If also the vitamin E content of the respective body or organ fluid is to be determined by the kit according to the invention, also the reagents and reference means required for this measurement (with the latter being, of course, identical when providing reference samples) are, of course, necessary.

In a further aspect, the present invention relates to a fertility determination by determining the vitamin E content of seminal and follicular fluids and correlating this content with a corresponding reference value, as well as to a corresponding kit for carrying out this method.

The method according to the invention, and the kit according to the invention, respectively, preferably are used for monitoring patients within the scope of fertilization methods, in particular in case of in vitro fertilization and intracytoplasmatic sperm injection. For a successful fertilization it is necessary to monitor very precisely the presence or absence of oocytes as well as their quality in the test persons, and to routinely monitor the sperm functionality, respectively, with a simple test.

A further preferred use of the test according to the invention or of the kit according to the invention, respectively, resides in determining the degree of maturity of oocytes or sperms.

Moreover, the method according to the invention, and the kit according to the invention, respectively, may be used for investigating fertility and reproduction disturbances and it is particularly well suited for broad screenings and for the systematic examination of large groups of persons.

A further particular field of application of the method according to the invention, and of the kit according to the invention, respectively, resides in the monitoring of pregnancies, starting with diagnosing the presence of a pregnancy (as a pregnancy test) as well as monitoring the pregnancy proper thereafter, in particular in the monitoring of the risk of negative effects of oxidative or radical substances, caused by a reduced content of afamin and vitamin E, respectively.

The present invention shall now be explained in more detail by way of the following examples and the drawing figures. Therein, FIG. 1 shows the correlation of afamin in follicular fluid of persons with or without an oocyte;

EXAMPLES

From patients who had been subjected to an ovulation induction for an in vitro fertilization (IVF) or intracytoplasmatic sperm injection (ICSI), follicles of various sizes were individually punctured by ultrasonographic means. The individual samples of the follucular fluid were tested for the presence or absence of oocytes, centrifuged, and stored for further tests. Blood samples were taken from these patients on the day of the follicle puncture and collected for the serum processing. The afamin concentration in the follicular fluid and in the serum were quantitated by means of sandwich-ELISA (using monoclonal antibodies). The determination of vitamin E in these samples was effected following protein precipitation and reversed phased HPLC. A qualitative analysis of afamin in follicular fluid and serum was effected by means of SDS-PAGE and immunoblotting.

Figure 1:
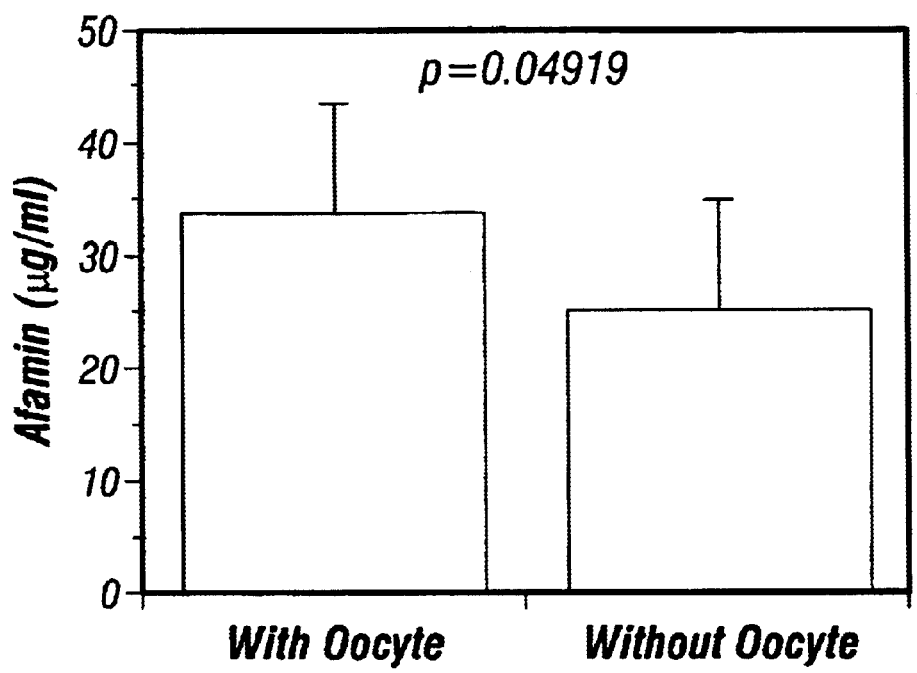

At first, 27 samples each were taken from patients with or without oocyte, respectively, and the afamin contents were determined. It was shown that the samples of patients with oocyte had a mean afamin concentration of 38.9 µg/ml, whereas the samples of patients without oocyte merely had 30.5 (FIG. 1). It was also shown that the afamin concentration in patients with oocyte was merely 30% higher than the "normal value" (=without oocyte).

Figure 2:
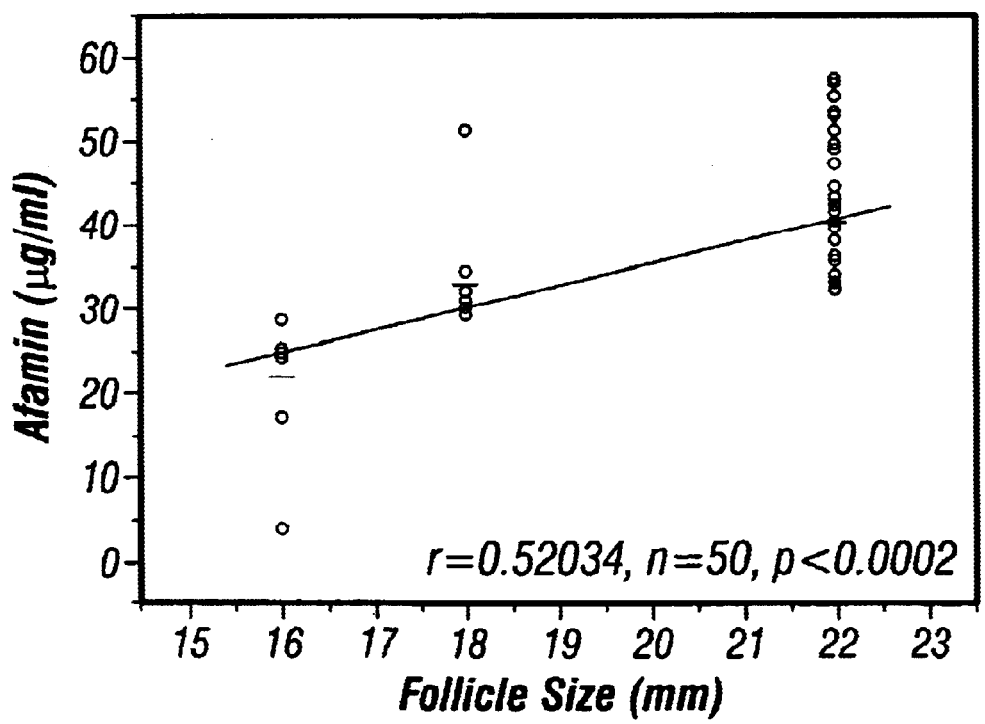
FIG. 2 shows the correlation of afamin concentration and follicle size.

Subsequently it was assayed whether and how the size of the follicle correlates with the afamin concentration. In doing so, the follicles were classified in three different types of size, and in FIG. 2 they were plotted against the afamin concentration determined. It was shown that also in this instance a clear correlation is found so that the afamin concentration constitutes a direct measure for the degree of maturity of an oocyte.

Figure 3:
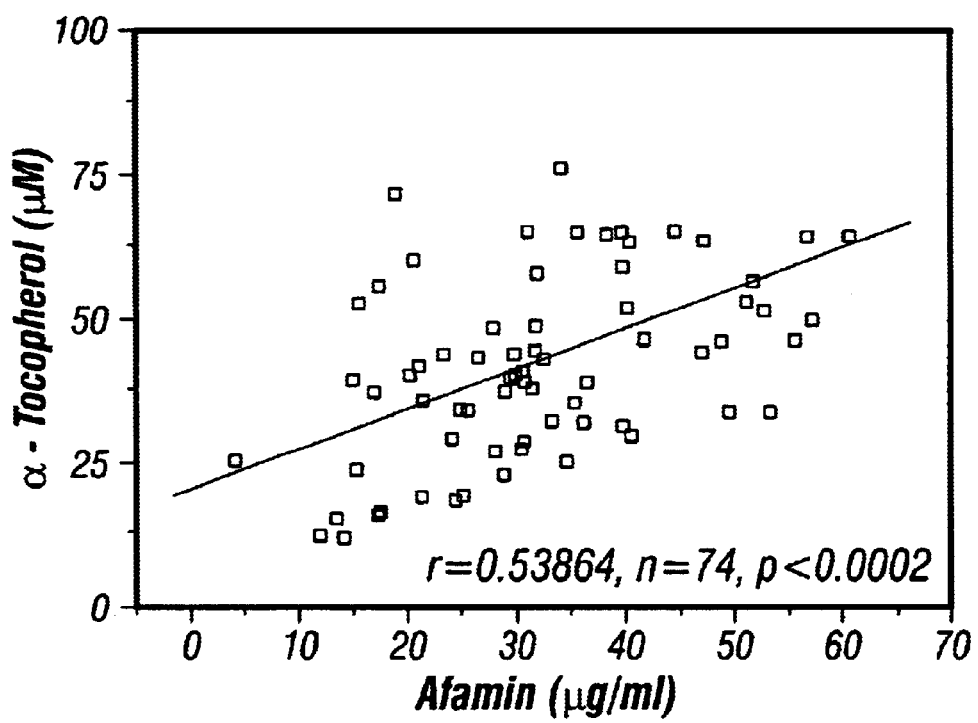
FIG. 3 shows the correlation of afamin and α-tocopherol concentration in follicular fluid.

From FIG. 3 it results that there also exists an unambiguous correlation between the vitamin E concentration and the afamin concentration in the follicular fluid, i.e., the higher the afamin concentration, the higher the vitamin E concentration.

In a further test series it was tested whether the correlation between presence/absence of oocytes, and the different degrees of maturity, respectively, of the oocytes proven for the follicular fluid also exists, e.g., in serum.

Figure 4:
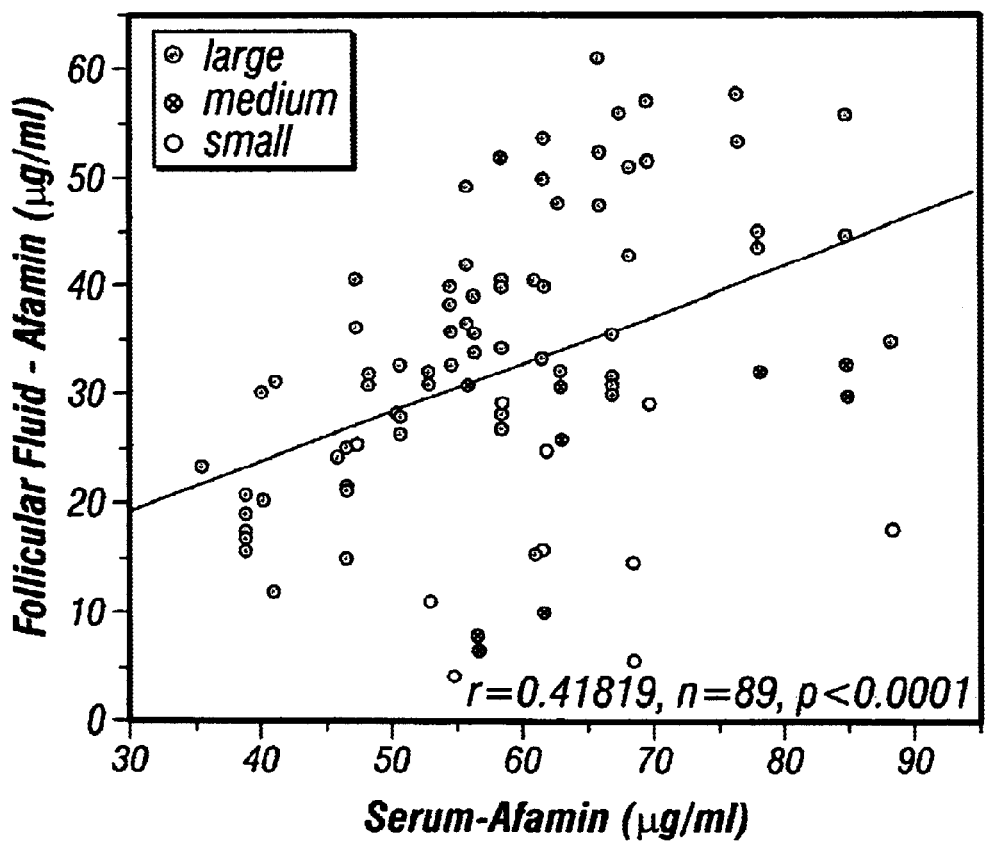
FIG. 4 shows the correlation of afamin and degree of maturity of oocytes in follicular fluid and serum, classified into large, medium-sized and small oocytes.

As is apparent from FIG. 4, the various degrees of maturity of oocytes can also be determined in serum via the afamin content.

Figure 5:
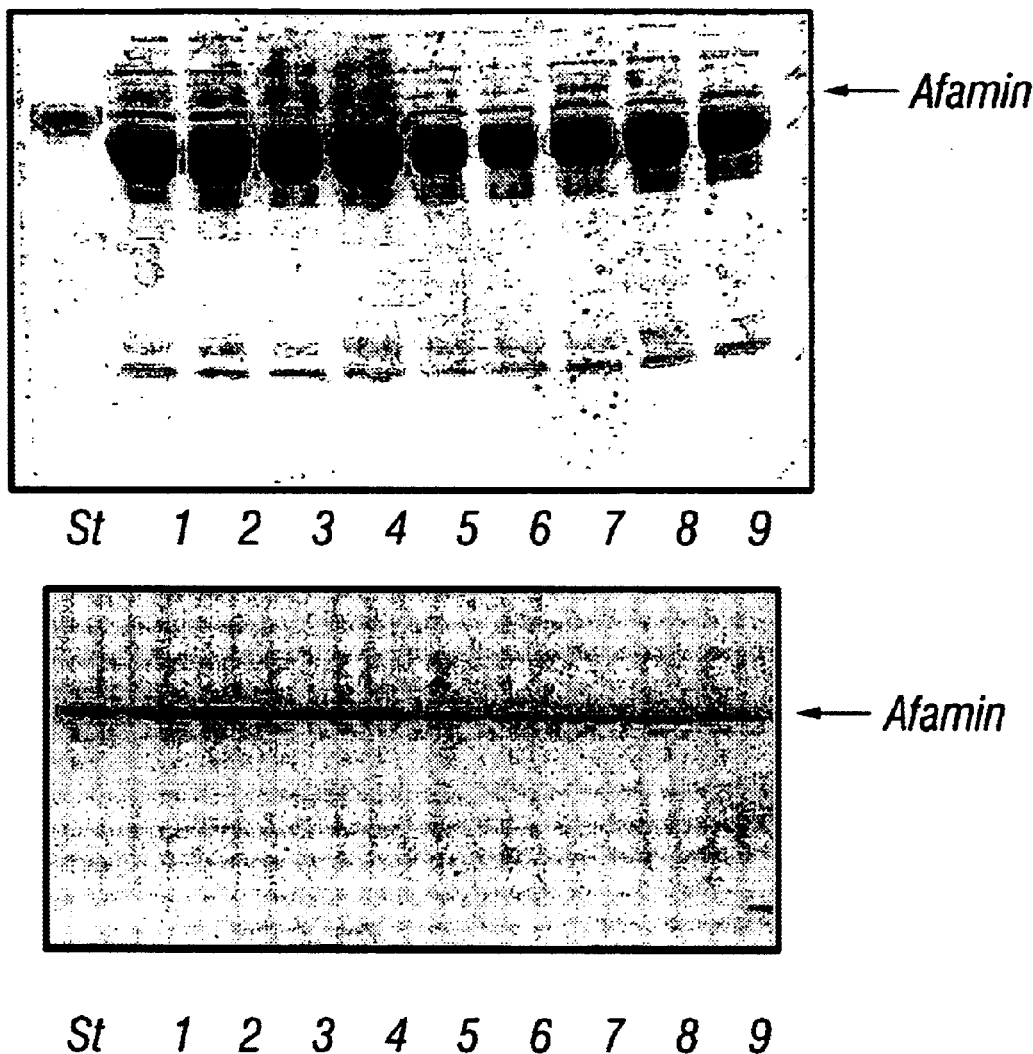
FIG. 5 is an SDS-PAGE with immunoblotting of 9 samples of follicular fluid.

In FIG. 5, a series of 9 different samples is illustrated by SDS-PAGE and immunoblotting with a monoclonal afamin antibody. In this instance, the determination of afamin can be effected via the standard (at the very left in FIG. 5).

Figure 6:
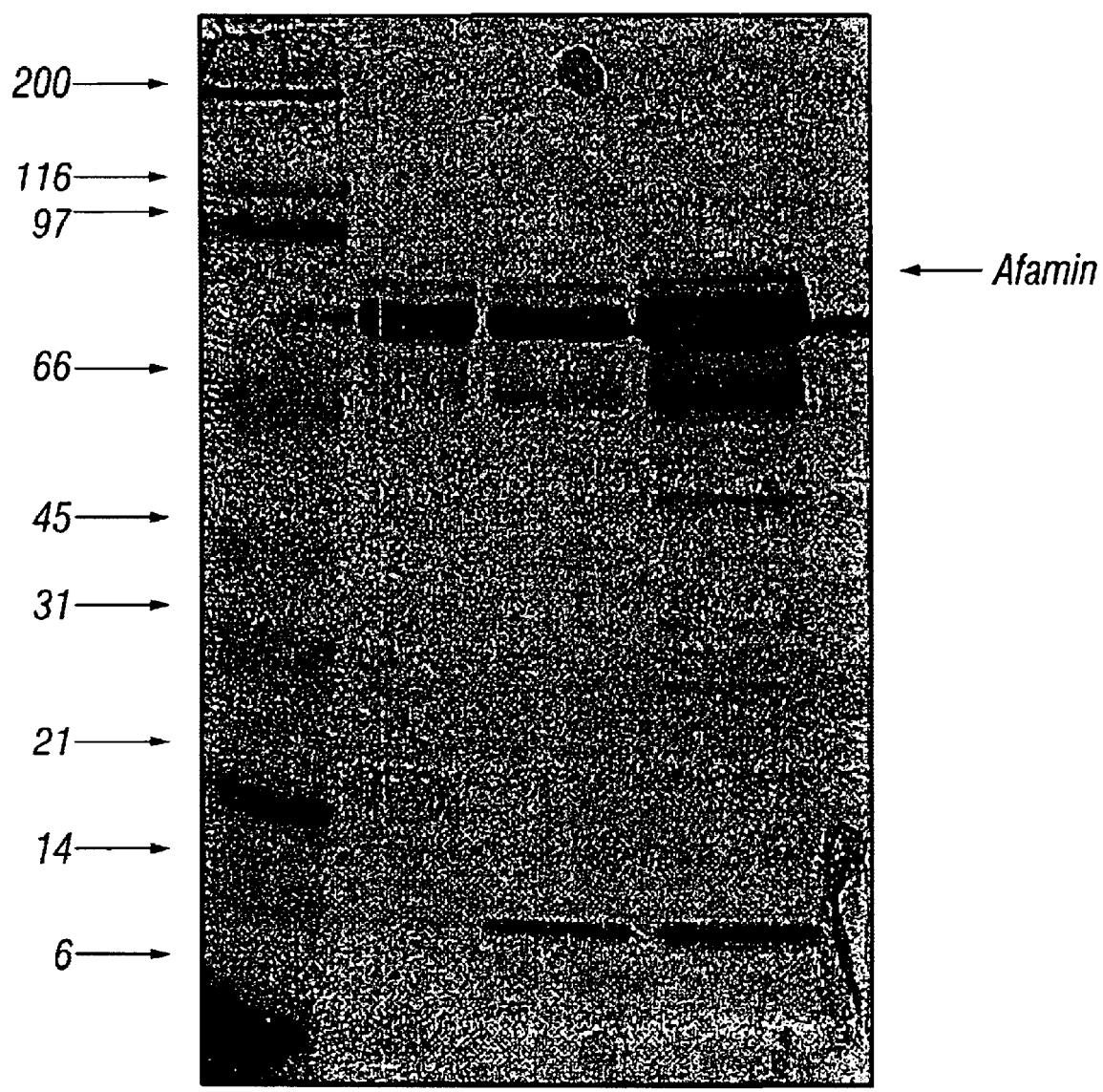
FIG. 6 is an SDS-PAGE with immunoblotting of 3 samples of liquor cerebrospinalis.

Finally, it was also tested whether the system according to the invention can also be used with cerebrospinal fluid (FIG. 6). As results from FIG. 6, also there it is possible to clearly determine the fertility properties due to the variance in the afamin contents.

What is claimed is:

1. A method of determining fertility and/or monitoring a pregnancy of a mammal comprising:
   taking a fluid from a mammal;
   determining an afamin content of the fluid; and
   comparing the afamin content determined with a reference value so as to:
   (a) determine the degree of maturity of oocytes of a mammal;
   (b) determine the degree of maturity of sperms of a mammal;
   (c) examine disturbances selected from the group consisting of fertility and reproduction disturbances in a mammal;
   (d) monitor a pregnancy of the mammal, or
   (e) monitor a patient during an intracytoplasmatic sperm injection procedure.

2. The method of claim 1, wherein the mammal is a human.

3. The method of claim 1, wherein the fluid taken from the mammal is a body fluid.

4. The method of claim 1, wherein the fluid taken from the mammal is an organ fluid.

5. The method of claim 1, wherein the fluid taken from the mammal is selected from a group consisting of serum, follicular, and seminal fluid.

6. The method of claim 1, wherein the reference value is the afamin content in a corresponding fluid from a normal patient.

7. The method of claim 1, wherein the afamin content is determined by an immunological method.

8. The method of claim 7, wherein the immunological method comprises using a monoclonal antibody.

9. The method of claim 1, further comprising determining a vitamin E content in the fluid taken from the mammal.

10. The method of claim 9, further comprising comparing the vitamin E content determined in the fluid with a vitamin E reference value.

11. The method of claim 1, further defined as a method of determining the fertility of the mammal.

12. The method of claim 11, wherein the reference value is determined in parallel with determining fertility.

13. The method of claim 1, further defined as a method of monitoring patients during a fertilization procedure.

14. The method of claim 13, wherein the fertilization procedure is an in vitro fertilization.

15. The method of claim 13, wherein the fertilization procedure is an intracytoplasmatic sperm injection.

16. The method of claim 1, further defined as a method of determining the degree of maturity of oocytes of the mammal.

17. The method of claim 1, further defined as a method of determining the degree of maturity of sperms of the mammal.

18. The method of claim 1, further defined as a method of examining disturbances selected from the group consisting of fertility and reproduction disturbances in the mammal.

19. The method of claim 1, further defined as a method of monitoring a pregnancy of the mammal.

20. The method of claim 1, further defined as comprising using a kit comprising:
   a reagent for detecting the afamin content of the sample; and
   an afamin reference.

21. The method of claim 20, wherein the kit further includes a vessel for receiving the sample of the fluid.

* * * * *